(12) United States Patent
Zhao et al.

(10) Patent No.: US 9,724,392 B2
(45) Date of Patent: Aug. 8, 2017

(54) IL-25 TREATMENT OF OBESITY AND METABOLIC DISORDERS

(71) Applicants: Aiping Zhao, Ellicott City, MD (US); Terez Shea-Donohue, Chevy Chase, MD (US)

(72) Inventors: Aiping Zhao, Ellicott City, MD (US); Terez Shea-Donohue, Chevy Chase, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 293 days.

(21) Appl. No.: 13/941,214

(22) Filed: Jul. 12, 2013

(65) Prior Publication Data

US 2014/0037578 A1   Feb. 6, 2014

Related U.S. Application Data

(63) Continuation of application No. PCT/US2012/021041, filed on Jan. 12, 2012.

(60) Provisional application No. 61/461,122, filed on Jan. 13, 2011.

(51) Int. Cl.
| | |
|---|---|
| *A61K 38/20* | (2006.01) |
| *A61K 38/19* | (2006.01) |
| *A61K 45/00* | (2006.01) |
| *A61K 45/06* | (2006.01) |
| *A61K 9/00* | (2006.01) |

(52) U.S. Cl.
CPC .............. *A61K 38/20* (2013.01); *A61K 45/06* (2013.01); *A61K 9/0019* (2013.01)

(58) Field of Classification Search
None
See application file for complete search history.

(56) References Cited

PUBLICATIONS

Emamaullee et al. (2009), Diabetes, 58, p. 1302-1311.*
Zunig et al. (2010), Journal of Immunology, vol. 185, p. 6947-6959.*
Vikram et al. (2003), Nutrition, vol. 19, p. 503-509.*
Gordon et al. (2010), Immunity, vol. 32, pp. 593-604.*
Sumarac-Dumanovic et al. (2009), International Journal of Obesity, vol. 33, pp. 151-156.*

* cited by examiner

*Primary Examiner* — Christine J Saoud
*Assistant Examiner* — Jegatheesan Seharaseyon
(74) *Attorney, Agent, or Firm* — Benjamin Aaron Adler (57) ABSTRACT

The present invention provides a method for reducing the weight of a subject, preventing weight gain in a subject, lowering blood glucose, or treating hepatic steatosis, comprising administering to a subject in need thereof a therapeutically effective amount of a pharmaceutical composition comprising interleukin-25 or IL-25-activated macrophages. In addition, the present invention provides a method of treating cachexia or promoting weight gain in a mammal in need of such treatment, comprising administering to the mammal a therapeutically effective amount of a pharmaceutical composition comprising an inhibitor or antagonist of interleukin-25 in a mammal in the treatment of cachexia.

7 Claims, 8 Drawing Sheets

IL-25 TREATMENT OF OBESITY AND METABOLIC DISORDERS

CROSS-REFERENCE TO RELATED APPLICATIONS

This application is a continuation under 35 U.S.C. §120 of pending international application PCT/US2012/21041, filed Jan. 12, 2012, which claims benefit of priority under 35 U.S.C. §119(e) of provisional application U.S. Ser. No. 61/461,122, filed Jan. 13, 2011, the entirety of which is hereby incorporated by reference.

FEDERAL FUNDING LEGEND

This invention was made with government support under DK083418 awarded by the National Institutes of Health. The government has certain rights in the invention.

BACKGROUND OF THE INVENTION

Field of the Invention

The present invention relates generally to the fields of obesity and metabolic disorders. More specifically, the present invention discloses the use of interleukin-25 to treat obesity and metabolic disorders including diabetes and hepatic steatosis.

Description of the Related Art

The incidence of obesity has increased dramatically worldwide and has risen to endemic level in U.S., with over one-third of the adult American population being obese. Multiple factors contribute to obesity including genetic predisposition, environmental, socioeconomic, and behavioral factors. In addition, obesity is one of the key etiological factors for many metabolic diseases such as diabetes, hypertension, heart disease. Obesity is accompanied with chronic low grade inflammation in adipose tissues, mainly due to the accumulated inflammatory cells (Th1/Th17 cells, macrophages, etc), which, together with adipocytes, release variety of proinflammatory cytokines/chemokines that contribute to the development of the metabolic syndrome and exacerbation of obesity.

Among the infiltrated inflammatory cells in adipose tissue, macrophages are involved in the development of obesity-associated tissue inflammation and metabolic dysfunction. Depending on the cytokine microenvironment, macrophages undergo distinct pathways of activation and display different phenotypes: the classically-activated macrophages (M1) that are induced by the Th1 cytokine and characterized by the production of nitric oxide (NO) through inducible nitric oxide synthase (NOS-2), and the alternatively-activated macrophages (M2) induced by Th2 cytokines, IL-4 and IL-13, and characterized by highly up regulated arginase I, mannose receptor (CD206), as well as the secretion of chitinase and "found in inflammatory zone" (FIZZ) family members as YM1, FIZZ1, and FIZZ23. Obese adipose tissue usually contains more macrophages or adipose tissue macrophages (ATMs) than lean adipose tissue. In addition, more of those adipose tissue macrophages in obese tissue exhibit M1, a pro-inflammatory phenotype, rather than M2, an anti-inflammatory phenotype, resulting in an increased production of pro-inflammatory cytokines such as IL-6 and TNFα, and less production of the anti-inflammatory cytokines such as IL-10 and TGF-β2.

Besides macrophages, various subsets of lymphocytes are also found in the stromal vascular fraction of adipose tissue. A recent study showed that there is a CD8+ T cell infiltration preceding the accumulation of macrophages in obese adipose tissue and these CD8+ T cells participate in macrophage differentiation, activation, and migration. CD4+ Th1 cells may also help recruit macrophages into adipose tissue and stimulate the M1 macrophage inflammatory activation. In addition, these CD4+ cells can respond to specific antigen generated in obese adipose tissue to produce inflammatory Th1 cytokines. Meanwhile, the number of T regulatory cells, which have inhibitory effects on inflammation, is usually decreased in obese adipose tissue. As a result of all these combined factors, large amount of pro-inflammatory cytokines are produced in adipose tissue and released to circulation, which in turn cause insulin resistance as well as other metabolic syndromes. IL-25, also called IL-17E, is a cytokine member of IL-17 family. While other members of the IL-17 family, especially IL-17A and IL-17F, have biological activities similar to Th1 inflammatory cytokines, IL-25 is involved primarily in the promotion of Th2 immunity, including allergy, asthma, and enteric nematode infection. Of equal importance is that IL-25 also inhibits pro-inflammatory Th1 and Th17 cytokine responses. Therefore, IL-25 is emerging as a key regulator of inflammation in the gut mucosa. It has been shown that IL-25 expression is up-regulated in the gut following nematode infection and the up-regulation depends upon IL-13 activation of STAT67. In addition, epithelial cells, but not immune cells, constitute the major source of IL-25 in the gut, implicating the important role of epithelium-derived factors in the induction of Th2 immunity.

Therefore, the prior art is deficient in methods of treating obesity, obesity related disorders and metabolic disorders. The present invention fulfills this long-standing need and desire in the art.

SUMMARY OF THE INVENTION

One aim of the present invention was to demonstrate the therapeutic effects of IL-25 against obesity and the metabolic syndrome including diabetes and hepatic steatosis.

Another aim of the present invention was to demonstrate the underlying mechanisms by which IL-25 regulates the body weight and glucose metabolism.

Another aim of the present invention was to demonstrate the contribution of macrophages in the effects of IL-25 on weight loss and glucose homeostasis. The present invention demonstrates that deficiency in IL-25 results in obesity, while exogenously-administered or endogenously-induced IL-25 has therapeutic effects against obesity and the associated metabolic syndrome including diabetes and hepatic steatosis. Furthermore, macrophage producing Th2 cytokines play an essential role in IL-25 effects against obesity.

The present invention provides a method for reducing the weight of a subject, preventing weight gain in a subject, lowering blood glucose, or treating hepatic steatosis, comprising administering to a subject in need thereof a therapeutically effective amount of a pharmaceutical composition comprising interleukin-25.

The present invention is further directed to a method of treating cachexia or promoting weight gain in a mammal in need of such treatment, comprising administering to the mammal a therapeutically effective amount of a pharmaceutical composition comprising an inhibitor or antagonist of interleukin-25 in a mammal in the treatment of cachexia.

The present invention is further directed to a method for reducing the weight of a subject, preventing weight gain, or treating metabolic syndrome by improving glucose metabolism and glucose homeostasis, in a subject, comprising administering to a subject in need thereof a therapeutically effective amount of a pharmaceutical composition comprising macrophages which have been treated with IL-25.

BRIEF DESCRIPTION OF DRAWINGS

FIGS. 4A-4C shows effects of IL-25 on blood glucose and hepatic GLUT4 expression.

FIGS. 5A-5B show the effects of IL-25 on the liver.

FIG. 7A-7D shows the effect of IL-25 on IL-13.

DETAILED DESCRIPTION OF THE INVENTION

As described in detail below, the present invention is directed to a method for reducing the weight of a subject, preventing weight gain in a subject, lowering blood glucose, and/or treating hepatic steatosis, comprising administering to a subject in need thereof a therapeutically effective amount of a pharmaceutical composition comprising interleukin-25 or IL-25-activated macrophages. The pharmaceutical composition may comprise one or more pharmaceutically acceptable carriers. Representative pharmaceutically acceptable carriers are described in detail infra. Generally, this composition of the present invention may be administered in a dose effective to reduce or prevent weight gain in a subject. Preferably, the composition is administered to the subject in an amount of from about 0.5 mg/kg/day to about 1 mg/kg/day. Representative subjects include a human, a cat or a dog. Preferably, the human is obese or overweight or has a body mass index of at least about 25 kg/m$^2$.

Without being limited to mechanism of action, it is expected that this composition increases the gene expression of IL-13, decreases the expression of TNFα, increases hepatic GLUT4 expression and increases activation of macrophages in, for example, epididymal fat and liver. This method may further comprise administering a therapeutically effective amount of a weight loss agent to maintain a reduced weight in the subject. This weight loss agent may be administered simultaneously or sequentially. Representative weight loss agents are selected include but are not limited to serotonin and noradrenergic re-uptake inhibitors, glucagon-like peptide-1 analogs, noradrenergic re-uptake inhibitors, selective serotonin re-uptake inhibitors, and intestinal lipase inhibitors.

In another embodiment of the present invention, there is provided a method of treating cachexia or promoting weight gain in a mammal in need of such treatment, comprising administering to the mammal a therapeutically effective amount of a pharmaceutical composition comprising an inhibitor or antagonist of interleukin-25 in a mammal in the treatment of cachexia. Conditions involving cachexia include but are not limited to aging, cancer, heart failure, lung disease, lung disease, liver failure, cirrhosis, stroke, rheumatoid arthritis, severe burn injury, kidney failure and HIV/AIDS. Representative inhibitors or antagonists of interleukin-25 include but are not limited to an antibody, an antibody fragment, a peptide, a polypeptide, an oligonucleotide, a small molecule and a combination thereof. For example, the inhibitor or antagonist of interleukin-25 may be a soluble IL-25 receptor such as IL17RB, an IL-25 antibody and an antagonistic IL-25 receptor antibody.

In another embodiment of the present invention, there is provided a method for reducing the weight of a subject, preventing weight gain, or treating metabolic syndrome by improving glucose metabolism and glucose homeostasis, in a subject, comprising administering to a subject in need thereof a therapeutically effective amount of a pharmaceutical composition comprising macrophages which have been treated with IL-25. Generally, the macrophages are selected from the group consisting of bone marrow-derived macrophages, peripheral blood-derived macrophages, peritoneal macrophages, and peritoneal exudate cells. Preferably, this composition is administered by intraperitoneal injection. A person having ordinary skill in this art could readily determine an optimum concentration of IL-25 treated macrophages to administer based on the desired results.

The following abbreviations were used herein: *N. brasiliensis, Nippostrongylus brasiliensis*; IL-4-/-, IL-4-deficient; IL-3 13-/-, IL-13-deficient; IL-25-/-, IL-25-deficient; STAT6-/-, STAT6-deficient; WT, wild type.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

DEFINITIONS

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The terms "comprise" and "comprising" are used in the inclusive, open sense, meaning that additional elements may be included.

The term "including" is used to mean "including but not limited to". "including" and "including but not limited to" are used interchangeably.

As used herein, the following terms and phrases have the meanings set forth below. Unless defined otherwise, all technical and scientific terms used have the same meaning as commonly understood to one of ordinary skill in the art.

As used herein, the term "suppress" or "suppressing" means partially or totally blocking stimulation, decreasing, preventing, delaying activation, inactivating, desensitizing, inhibiting, or down regulating a measurable change in cell function, for example change in IL-25 signaling. Suppressing a measurable change in cell function is achieved when the activity value assigned to the cell function relative to the control is 50-80%, optionally 25-50% or 0-25%, where control samples are assigned a relative activity value of 100%. Suppressing a measurable change in cell function can be achieved by various strategies. For example, suppressing IL-25 signaling can be achieved by blocking IL-25 and IL-25 receptor interaction or suppressing IL-25 receptor expression.

The term "IL-25 receptor" as used herein means a receptor or a receptor complex mediating IL-25 signaling. IL-25 signaling requires two receptors, IL17RB and IL17RA, which may form a heteromeric complex. IL-25 binds to IL17RB with high affinity, whereas IL17RA does not bind IL-25 but is required for activating signaling pathways upon ligand binding. Thus, "IL-25 receptor" contemplates both IL17RB and IL17RA. The term "IL17RB" (IL-17BR, CRL4, EVI27, IL17RH1, or MGC5245) as used herein means "interleukin 17 receptor B", a polypeptide having an amino acid sequence according to GenBank Acc. No. NP.sub.-061195, the product of the human IL17RB receptor gene, and include all of the variants, isoforms and species homologs of IL17RB. Both IL-25 and IL-17B are ligands for IL17RB, but the receptor binds IL-25 with higher affinity. The term "IL17RA", (CD217, IL17R, CDw217, IL-17RA, hIL-17R, or MGC10262) as used herein means "interleukin 17 receptor A", a polypeptide having an amino acid sequence according to GenBank Acc. No. NP.sub.-055154, the product of the human IL17RA receptor gene, and include all of the variants, isoforms and species homologs of IL17RA. Variants of IL17RB and IL17RA also include soluble mature receptors.

The term "IL-25" or "IL-25 polypeptide" (IL17E, or IL-17E) as used herein means "interleukin-25", a polypeptide having a sequence according to GenBank Acc. No. NP.sub.-073626 or NP.sub.-758525, the product of the human IL-25 gene, and include all of the variants, isoforms or species homologs of IL-25.

The term "IL-25-activated macrophages" as used herein means macrophages treated with IL-25 in vitro or in vivo. Macrophages can be differentiated from monocytes or isolated from tissues. Exemplary are bone marrow-derived macrophages, peripheral blood-derived macrophages, peritoneal macrophages, and peritoneal exudate cells.

The term "IL-25 signaling" as used herein means the processes initiated by IL-25 or a second IL-25 receptor ligand interacting with the IL-25 receptor on the cell surface, resulting in measurable changes in cell function. IL-25 receptor complex includes I17RB and IL17RA, and ligand binding activates downstream signal transduction pathways for example adaptor molecule TRAF6, JNK/p38 and ERK, and NF-.kappa.B, leading to the production of cytokines and chemokines. IL-25 signaling can be measured for example by assessing the amount of cytokines and chemokines produced upon induction with an IL-25 receptor ligand, for example measuring production of CXCL-8, IL-6, G-CSF, MCP-1, MIP-1.alpha., RANTES, or CCL2. IL-25 signaling can also be assessed by functional assays measuring for example effect of IL-25 receptor ligand on cell proliferation or differentiation, or using reporter genes and reporter gene constructs operatively linked to a promoter sensitive to NF-.kappa.B. Examples of such promoters include those for IL-6, IL-8 and IL-12 p40. Activation of intracellular kinases for example JNK/p38 can be measured by phospho-antibodies, and assaying secreted molecules or measuring cell proliferation or differentiation can be done using enzyme-linked immunosorbent assay (ELISA) or a spectrum of bioassays. The methods and suitable readout systems are well known in the art and are commercially available.

The term "ligand" refers to a peptide or polypeptide, a small molecule, or an oligonucleotide that binds to, or complexes with the IL-25 receptor or variant thereof. The ligand may be an antagonist, inhibitor, suppressor, agonist, stimulator or activator, or the like, of IL-25 receptor. Exemplary ligands are IL-25 and IL-17F.

IL-25 signaling can be inhibited using various agents and inhibitors of IL-25 signaling. The agents and inhibitors can target IL-25 and/or IL-25 receptor, or specifically inhibit the interaction of IL-25 with the IL-25 receptor. Such agents and inhibitors are, for example, antibodies or antibody fragments against IL-25 or IL-25 receptor, recognizing extracellular portions of the receptor polypeptides, antisense or siRNA molecules designed against IL-25 or IL-25 receptor genes, or soluble IL-25 receptors comprising soluble IL17RB or soluble IL17RA receptor polypeptides. Peptides, oligonucleotides or small molecules blocking interaction between IL-25 and the IL-25 receptor can be used. Such agents and inhibitors can also be peptides, proteins, fusion proteins, or small molecules that prevent interaction of IL-25 with the IL-25 receptor. Agents inhibiting IL-25 have been described, e.g., in U.S. Pat. No. 6,562,578 to Gorman and U.S. Pat. No. 6,635,443 to Shi.

It is possible to modify the structure of the polypeptides or fragments used as agents to inhibit IL-25 signaling for such purposes as enhancing substrate specificity, stability, solubility, and the like. For example, a modified polypeptide can be produced in which the amino acid sequence has been altered, such as by amino acid substitution, deletion, or addition. It is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine); (3) aliphatic (glycine, alanine, valine, leucine, isoleucine, serine, threonine), with serine and threonine optionally being grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The agent inhibiting IL-25 signaling can be conjugated to a second polypeptide to form a fusion protein that can confer desirable properties, for example increased stability. Exemplary fusion proteins can be formed by conjugating together a soluble mature IL17RB and an alternative scaffold such as designed ankyrin repeat protein (DARPins), MIMETIBODY™ construct, or other protein domains. Proteins, peptides or fusion proteins may generally be generated using either recombinant nucleic acid methods or by chemical synthesis methods well known in the art. A MIMETIBODY™ construct has the generic formula (I): $(Bp-Lk-V2-Hg-C_{H2}-C_{H3})_{(t)}$, (I) where Bp is a peptide or polypeptide capable of binding a molecule of interest, Lk is a polypeptide or chemical linkage, V2 is a portion of a C-terminus of an immunoglobulin variable region, Hg is at least a portion of an immunoglobulin variable hinge region, $C_{H2}$ is an immunoglobulin heavy chain $C_{H2}$ constant region and $C_{H3}$ is an immunoglobulin heavy chain $C_{H3}$ constant region, and t is independently an integer of 1 to 10.

The term "agent" as used herein refers to polypeptides, peptides or proteins, fusion proteins, peptidomimetics, antibodies, antibody fragments, nucleic acids, oligonucleotides, synthetic oligonucleotides, small molecules and the like that inhibit IL-25 signaling. The agent can be identified using assays measuring IL-25 signaling, which are described above. Examples of agents include a soluble mature IL17RB, IL-25 polypeptide, IL-25 antibody, antagonistic IL-25 receptor antibody, or antagonist IL17RB antibody.

The term "modulator" as used herein means a molecule or preparation that is believed to provide a therapeutic benefit in humans or other animals and is believed to provide that therapeutic benefit, in part, through activating or suppressing IL-25 signaling. The term "modulator" includes inhibitors and activators. "Inhibitors" are agents that partially or totally block stimulation, decrease, prevent, delay activation, inactivate, desensitize or down regulate a measurable process in a cell, for example IL-25 signaling, e.g., antagonists or antagonistic. Activators are agents that stimulate, increase, open, activate, facilitate, enhance activation, sensitize, or up regulate a measurable process in a cell, for example IL-25 signaling, e.g., agonists. For example, modulator of IL-25 signaling can interact directly with IL-25 or components of the IL-25 receptor, usually binding to IL-25 receptor, any component of the IL-25 receptor, or IL-25 receptor ligand with an affinity constant of about $10^{-6}$ M, about $10^{-8}$ M, about $10^{-9}$ M, or about $10^{-10}$ M. The modulator can also modulate IL-25 signaling indirectly, for example modulating IL-25 receptor expression. Modulators include antibodies, antibody fragments, peptides, polypeptides, oligonucleotides, small chemical molecules and the like.

The term "antibody" as used herein refers to a molecule specifically binding to an antigen, and includes dimeric, trimeric and multimeric antibodies, and chimeric, humanized and fully human antibodies. An antibody may be a whole antibody or a functional fragment of an antibody molecule, such as a fragment retaining at least its antigen binding function, and include Fab, F(ab'), F(ab')$_2$, scFv, dsFv, and diabodies. For example, antibody fragments may be obtained using proteolytic enzymes (e.g., a whole antibody is digested with papain to produce Fab fragments, and pepsin treatment results in the production of F(ab')$_2$ fragments). Techniques for the preparation and use of the various antibodies are well known in the art. For example, fully human monoclonal antibodies lacking any non-human sequences can be prepared from human immunoglobulin transgenic mice or from phage display libraries.

The term "Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

As used herein, an "insulin resistance disorder," refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy; nephropathy, glomerulonephritis, glomerulosclerosis, nephrotic syndrome, hypertensive nephrosclerosis some types of cancer, such as endometrial, breast, prostate, and colon, complications of pregnancy, poor female reproductive health, such as menstrual irregularities, infertility, irregular ovulation, polycystic ovarian syndrome, lipodystrophy, cholesterol related disorders, such as gallstones, cholecystitis and cholelithiasis, gout, obstructive sleep apnea and respiratory problems, osteoarthritis, and prevention and treatment of bone loss, e.g. osteoporosis.

"Obese" individuals or individuals suffering from obesity are generally individuals having a body mass index (BMI) of at least 25 or greater. Obesity may or may not be associated with insulin resistance.

A "patient" "individual," "subject" or "host" refers to either a human or a non-human animal.

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "mammal" is known in the art, and exemplary mammals include humans, primates, bovines, porcines, canines, felines, and rodents (e.g., mice and rats).

The term "pharmaceutically-acceptable salt" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The terms "systemic administration", "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

"Treating" a condition or disease refers to curing as well as ameliorating at least one symptom of the condition or disease.

Kits of the Invention

Interleukin-25 for use as described herein may be contained in a kit. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional component may be separately placed. However, various combinations of components may be comprised in a vial.

The kits of the present invention also will typically include a means for containing the molecule and any other reagent containers in close confinement for commercial sale. Such containers may include injection or blow molded plastic containers into which the desired vials are retained. Such kits will generally contain, in suitable container means, a pharmaceutically acceptable formulation that can be administered to a mammal. The kit may have a single container means and/or it may have distinct container means. When the components of the kit are provided in one and/or more liquid solutions, the liquid solution is an aqueous solution, with a sterile aqueous solution being particularly preferred. The interleukin-25 useful as an anti-obesity agent may also be formulated into a syringeable composition. In which case, the container means itself may be a syringe, pipette, and/or other such like apparatus, from which the formulation may injected or otherwise administered to a mammal, and/or even applied to and/or mixed with the other components of the kit. Examples of aqueous solutions include, but are not limited to ethanol, DMSO and/or Ringer's solution. In certain embodiments, the concentration of DMSO or ethanol that is used is no greater than 0.1% or (1 ml/1000 L).

The components of the kit may also be provided as a dried powder(s). When reagents and/or components are provided as a dry powder, the powder can be reconstituted by the addition of a suitable solvent. It is envisioned that the solvent may also be provided in another container means. The container means will generally include at least one vial, test tube, flask, bottle, syringe and/or other container means, into which the interleukin-25 is suitably allocated. The kits may also comprise a second container means for containing a sterile, pharmaceutically acceptable buffer and/or other diluent. The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the agents or compounds within the body of a mammal. Such an instrument may be a syringe, pipette, forceps, and/or any such medically approved delivery vehicle.

EXAMPLE 1

Mice

BALB/c, C57BL/6, and severe compromised immunodeficiency (SCID) mice were purchased from the Small Animal Division of the National Cancer Institute or Jackson laboratory (Bar Harbor, Me. 04609). These studies were conducted in accordance with principles set forth in the Guide for Care and Use of Laboratory Animals, Institute of Laboratory Animal Resources, National Research Council, Health and Human Services Publication (National Institutes of Health 85-23, revised 1996), and the Beltsville Animal Care and Use Committee, 2003.

EXAMPLE 2

Administration of IL-25

For administration of cytokine, mice (n=5/group) were injected i.v. with 0.7 μg of mouse recombinant IL-25 (R&D Systems, Minneapolis, Minn.) in 100 μl of saline daily for 7 days or as indicated otherwise. Control mice were given an injection of 35 μg BSA. The amount of cytokine administered was based on the minimum dose of IL-25 that induced a prominent Th2 immune response.

EXAMPLE 3

Glucose Tolerance Test

An oral glucose tolerance test was carried out in mice after overnight fasting. Mice were administrated orally with 25% glucose (4 ml/g body weight) in saline by gavage. Blood glucose level was monitored from tail vein blood samples at 0, 30, 60, and 120 minutes after glucose administration.

EXAMPLE 4

Liposome-Mediated Macrophage Depletion and Inhibition of Arginase Activity In Vivo Briefly, clodronate- (Cl2MDP) or control PBS-containing liposomes were administrated (0.2 ml, i.v.) to mice to deplete macrophages. Liposomes were generated using phosphatidylcholine (LIPOID E PC; Lipoid GmbH, Ludwigshafen, Germany) and cholesterol (Sigma, St. Louis, Mo.). Clodronate containing liposomes were obtained from Roche Diagnostics GmbH (Mannheim, Germany). For the experiment to determine the role of macrophages in the IL-25 effects on body weight loss in mice, clodronate containing liposomes administration began 5 days before the IL-25 treatment and continued every other day throughout.

EXAMPLE 5

RNA Extraction, cDNA Synthesis and Real-Time Quantitative Polymerase Chain Reaction (qPCR)

Total RNA was extracted from intestine whole tissue or from LCM samples. Total RNA was extracted with TRIZOL® Reagent, a monophasic solution of phenol, guanidine isothiocyanate, and other proprietary components, (Invitrogen, Grand Island, N.Y.) as per the manufacturer's instructions. RNA integrity, quantity, and genomic DNA contamination were assessed using the Agilent Bioanalyzer 2100 and RNA 6000 LABCHIP® kit, including RNA dye concentrate, RNA 6000 Marker and RNA 6000 gel matrix (Agilent Technologies, Palo Alto, Calif.). Only those RNA samples with 28S/18S ratios between 1.5 to 2 and no DNA contamination were studied further. RNA samples (2 mg) were reverse-transcribed to cDNA using the First Strand cDNA Synthase Kit (MBI Fermentas, Hanover, Md.) with random hexamer primer. Real-time quantitative PCR was performed on an iCycler detection system (Bio-Rad, CA). PCR was performed in a 25 ml volume using SYBR® Green supermix, a ready to use reaction master mix containing antibody-mediated hot-start Taq DNA polymerase, dNTPs, $MgCl_2$, SYBR® Green I dye, enhancers, stabilizers and fluorescein (Bio-Rad, Hercules, Calif.). Amplification conditions were: 95° C. for 3 min, 50 cycles of 95° C. for 15 s, 60° C. for 15 s, and 72° C. for 20 s. The fold-changes in mRNA expressions for targeted genes were relative to the respective vehicle groups of mice after normalization to 18s rRNA. 18s rRNA was selected for the internal standard in the real-time PCR, based on studies showing that there were no significant differences in the 18s rRNA level among the different groups of samples (infected and uninfected). In addition, a search of the literature indicates that 18s rRNA is among the most common endogenous standards. Primer sequences were designed by using Beacon Designer 5.0 (Premier Biosoft International, Palo Alto, Calif.), and synthesized by the Biopolymer Laboratory of the University of Maryland.

EXAMPLE 6

Bone Marrow-Derived Macrophages

Mouse femurs and tibiae were isolated and flushed with medium to collect monocytes. Macrophages were generated by 7 days' differentiation from bone marrow monocytes with M17 CSF.

EXAMPLE 7

Adoptive Transfer of Macrophages

Bone marrow-derived macrophages were stimulated with IL-25 (50 μg/ml) for 72 hours, harvested, and adoptively transferred to mice (i.p, 2×106 cells/mouse).

EXAMPLE 8

Data Analysis

Agonist responses were fitted to sigmoid curves (Graphpad, San Diego, Calif.). Statistical analysis was performed using one-way ANOVA followed by Neuman-Keuls test to compare the responses and gene expression among the different treatment groups.

EXAMPLE 9

Establishment of a Physiologically Relevant Mouse Model of Obesity-High Fat Diet-Induced Obesity Several experimental animal models of obesity has been developed and used for various purposes, while high fat diet-induced obesity represents the most physiologically relevant model and was used for current study. Male, 4-week-old C57BL/6 mice were kept on high-fat diet (HFD) for 16 weeks and the body weight and food intake were monitored weekly. A separate group of mice fed with normal control diet (NCD) were used as controls. Starting at the sixth week, mice on high-fat diet gained significantly more body weight than that on normal control diet, and that weight gain trend continued during the entire course of the high-fat diet feeding. By 13th week, mice on the high-fat diet weighed average 46.8±1.8 g while the mice on normal control diet weighed average 31.4±0.7 g. The obese mice had significant higher fasting blood glucose level than that of lean mice (obese verse lean, 180.3±7.9 verse 94.6±9.0).

Figure 1:
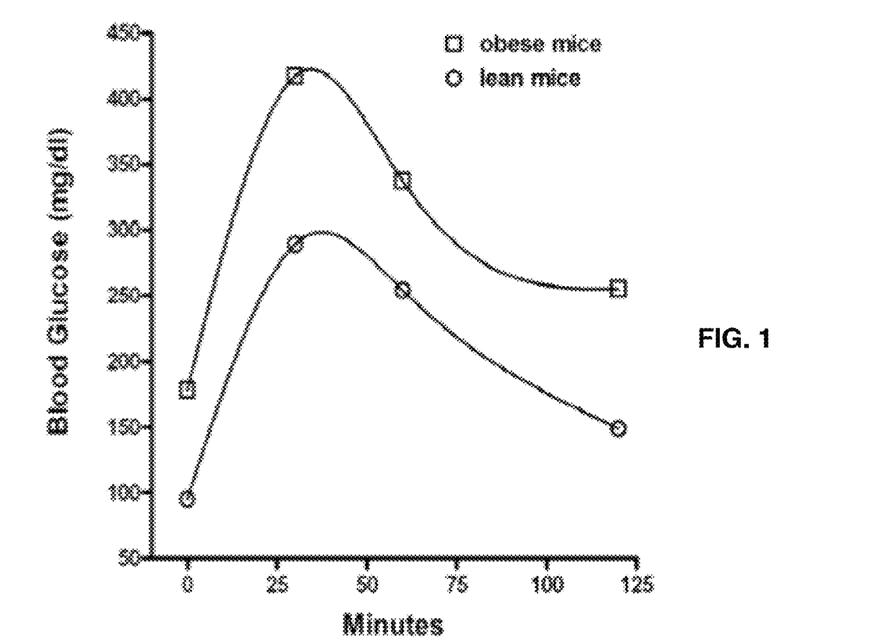
FIG. 1 shows that obese mice exhibited impaired glucose tolerance. An oral glucose tolerance test (OGTT) was performed in mice by oral administration of glucose and blood glucose was measured at the indicated time points. *$p<0.05$ vs lean mice, n=10 per group.

To further determine whether the obese mice develop abnormal glucose metabolism, glucose tolerance tests were carried out in both obese and lean mice by oral administration of glucose through gavage and monitoring the changes in blood glucose level. Indeed, the blood glucose levels of obese mice were greater than that of lean mice at all the time points monitored (FIG. 1). These results indicate that the obese mice exhibited glucose intolerance or insulin resistance.

EXAMPLE 10

Administration of IL-25 Induced Significant Loss of Body Weight and Adipose Tissue Mass in Obese Mice Obese mice are generally accompanied with low grade chronic inflammation in adipose tissues, and are characterized by increased production/circulating levels of pro-inflammatory Th1 and Th17 cytokines. Given the potent anti-inflammatory properties of IL-25, whether using exogenous IL-25 to count-regulate the Th1-dominant inflammation would influence the body weight and the associated metabolic syndrome was determined.

Figure 2:
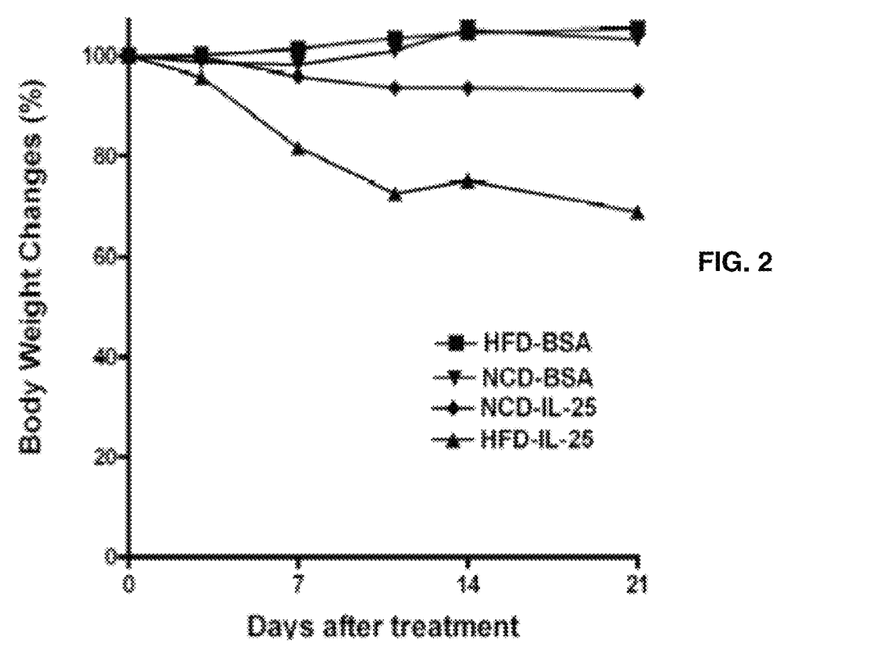
FIG. 2 shows body weight changes during the course of treatment. Mice were feed with high-fat (HFD) or normal control (NCD) diet for 16 weeks and were then treated with IL-25 or BSA. Body weights were monitored every few days after the treatment until the end of experiment. *$p<0.05$ vs Day 0, n=5 per group

At the sixteenth week on the diet, obese mice were re-grouped and then administered either IL-25 (HFD-IL-25) or BSA (HFD-BSA) using the following schedule: a daily injection (0.7 μg/mouse in 0.1 ml PBS, i.p.) for 5 days followed by one injection every other day for an additional 16 days. Age-, sex-matched mice fed with normal control diet were used as controls and were also injected with either IL-25 (NCD-IL-25) or BSA (NCD-BSA). The weight loss in obese mice treated with IL-25 was notable at as early as the 3rd day post-injection. The weight loss trend continued throughout the entire course of treatment, and these mice lost more than 30% of their body weight by the time they were euthanized (FIG. 2), whereas HFD-BSA mice gained a small but significantly body weight at the end of experiment (106±2% of initials). It is noteworthy that the body weight of the lean mice also changed slightly, with a small gain for BSA-treated mice but a small loss for IL-25-treated ones (FIG. 2).

Food intake was also monitored during the course of the experiment. Both IL-25-treated HFD and NCD mice consumed significant less food than the ones treated with BSA, especially during the first week of treatment when the weight loss was most dramatically. From 10 days post-treatment on, the food intake in IL-25-treated mice returned to normal level and was not different from that of BSA-treated animals, while the weight loss in HFD-IL-25 continued. These data indicate that reduced food intake, together with other potential factors, may contribute to IL-25-induced weight loss.

Figure 3:
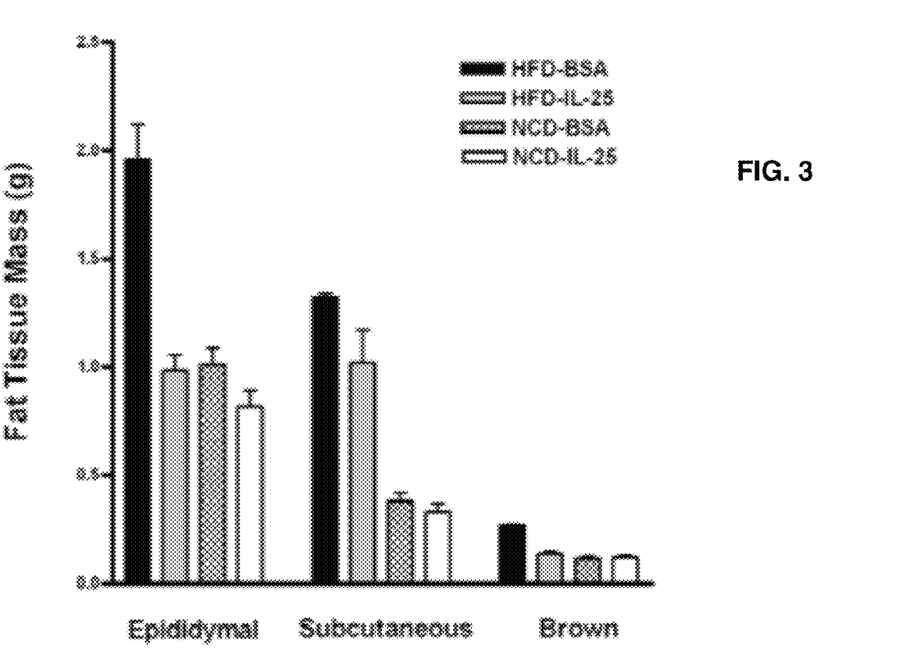
FIG. 3 shows that IL-25-induced changes of adipose tissue mass in obese and lean mice. $P<0.05$ vs the respective BSA-treated mice, n=5 per group.

After the mice were euthanized, the major organs were collected for mass comparison and molecular analysis. Most of the major organs in obese mice were proportionally larger than that in lean mice, including liver, heart, kidney, spleen, and adipose tissue (subcutaneous, epididymal, and brown fat). In obese mice, IL-25 treatment resulted in significant adipose tissue mass loss compared with BSA treatment (FIG. 3), while the weights of other major organs were comparable between the two treatments, with the exception that splenomegaly was observed in all IL-25-treated mice. IL-25 treatment in lean mice also caused slight, significant mass loss of visceral and subcutaneous fats (FIG. 3), despite the body weights were similar between two treatments (FIG. 2).

Additional evidence on the role of IL-25 in regulating body weight came from the mice with IL-25 deficiency. C57BL/6 WT male mice weight ~41 grams at the age of 70 week old, while 62 week old male IL-25KO mice weigh 55.13±0.98 grams (n=3) that is dramatically heavier than WT.

EXAMPLE 11

IL-25-Induced Weight Loses in Obese Mice was Associated with Improved Glucose Metabolism As described above, obese mice displayed impaired glucose metabolism including higher fasting blood glucose level and reduced glucose tolerance. To determine whether IL-25-induced weight loss was accompanied with any improvement in glucose homeostasis, the fasting blood glucose level was monitored and glucose tolerance test was performed by orally feeding glucose in mice after exposure to IL-25.

Figure 4A:
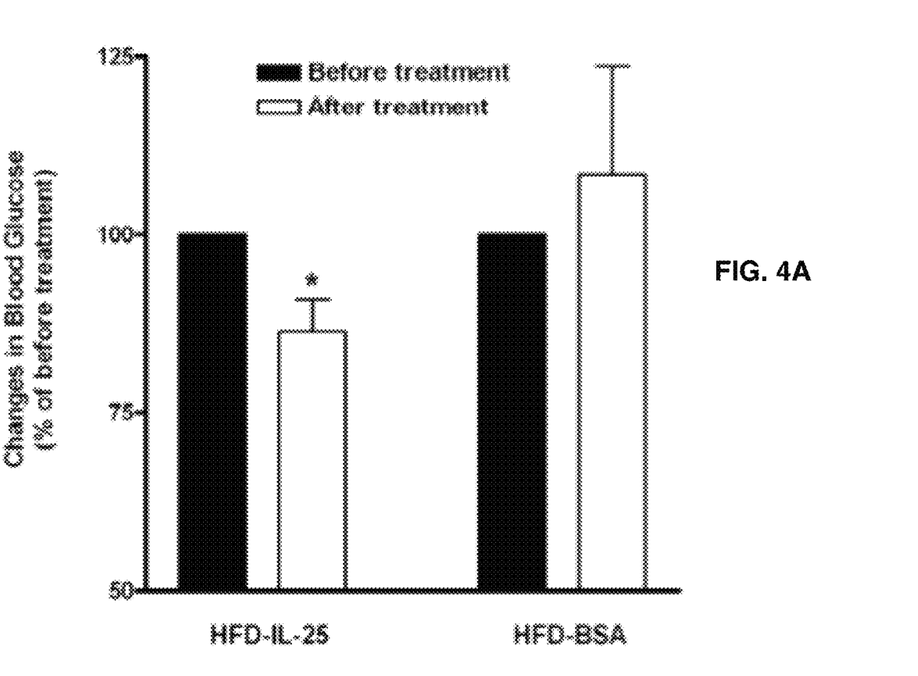
FIG. 4A: IL-25-induced decrease in blood glucose level in obese mice. *$p<0.05$ vs Before treatment, n=5 per group
Figure 4B:
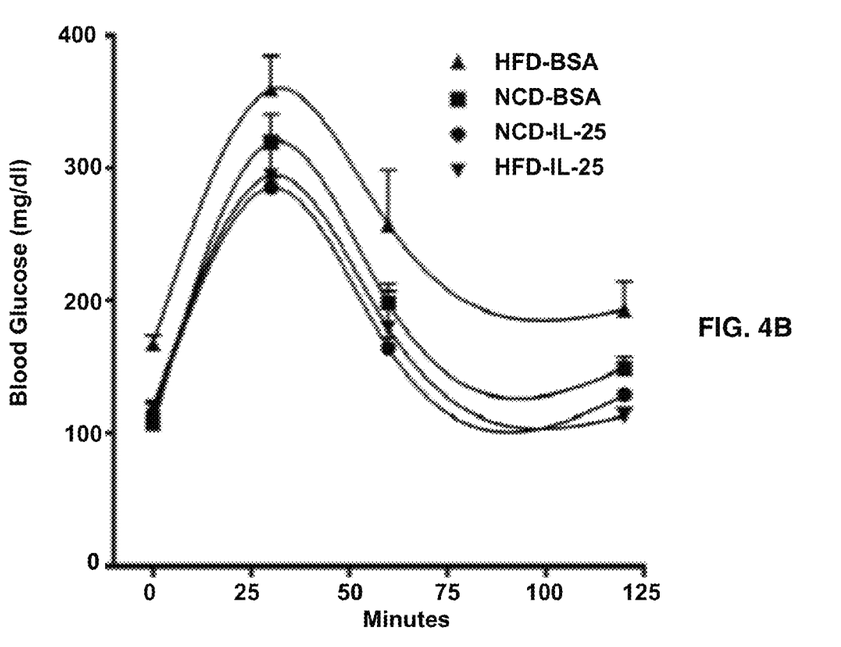
FIG. 4B: IL-25-induced improvement of glucose tolerance. An oral glucose tolerance test was performed in mice by oral administration of glucose and blood glucose level was measured at the indicated time points. *$P<0.05$ vs HFD-IL-25, n=5 per group.

In obese mice, IL-25 treatment significantly lowered the fasting blood glucose level while BSA had no effect (FIG. 4A). The blood glucose levels of normal control diet lean mice were not affected by either IL-25 or BSA treatment. In addition, HFD obese mice treated with IL-25 had significant improved glucose tolerance, indicated by the lower blood glucose levels at all time points examined after oral administration of bulk glucose comparing with the ones treated with BSA, whereas virtually identical clearance curves of blood glucose were observed between the normal control diet lean mice injected with IL-25 and BSA (FIG. 4B).

Figure 4C:
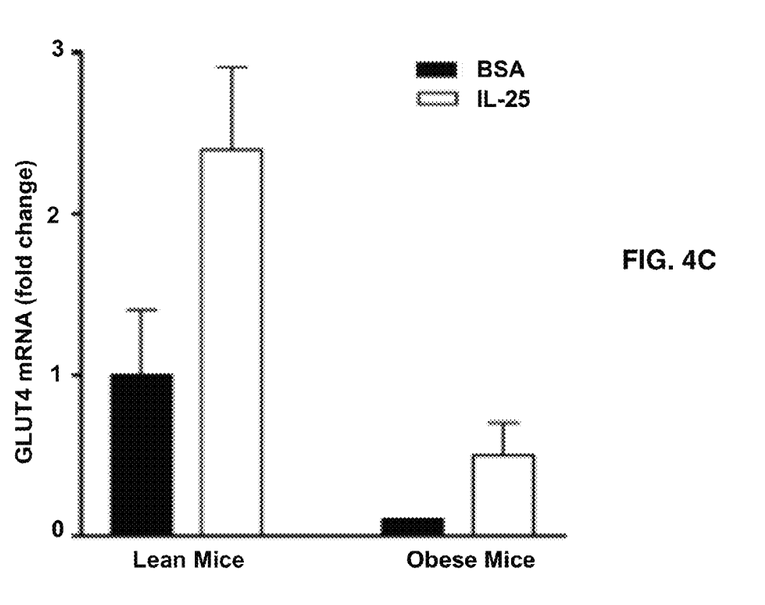
FIG. 4C: IL-25 up-regulated the hepatic GLUT4 expression. *$p<0.05$ vs BSA, *$p<0.05$ vs Lean, n=5 per group.

The mechanism through which IL-25 exerts the beneficial effects on glucose metabolism was further explored by examining the gene expression of GLUT4, an insulin-sensitive glucose transporter important for glucose homeostasis. Consistent with previous reports, obesity induced a down-regulation of GLUT4 in both adipose tissue and liver (FIG. 4C). Interestingly, IL-25 treatment increased the hepatic GLUT4 expression in both obese and lean mice, and restored the GLUT4 of obese mice up to the level of lean mice treated with BSA (FIG. 4C), implying that IL-25 may act through GLUT4 to regulate glucose metabolism.

EXAMPLE 12

Exogenous IL-25 Attenuated the Hepatic Steatosis in Obese Mice

Figure 5A:
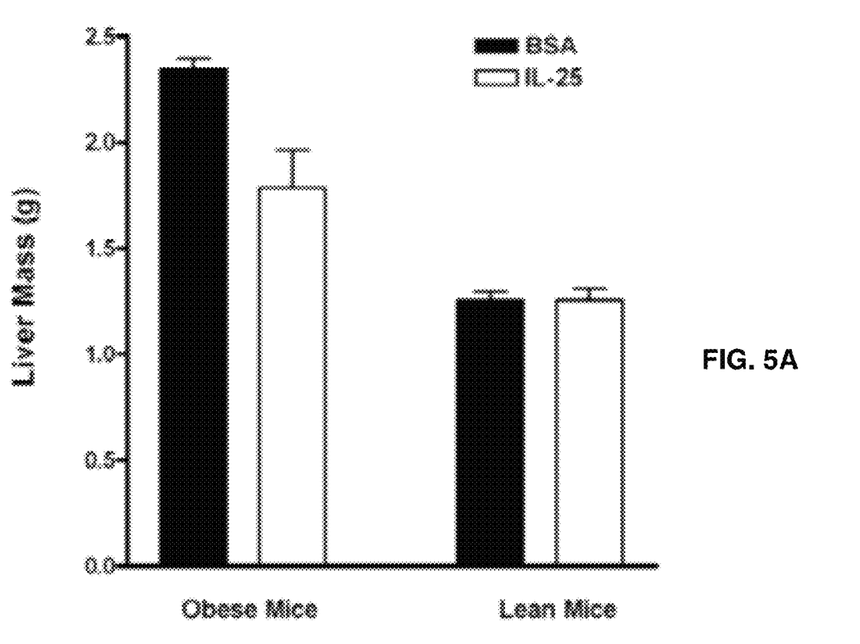
FIG. 5A: Obese mice had enlarged liver, whereas IL-25 treatment induced liver mass decrease in obese, but not lean, mice.
Figure 5B:
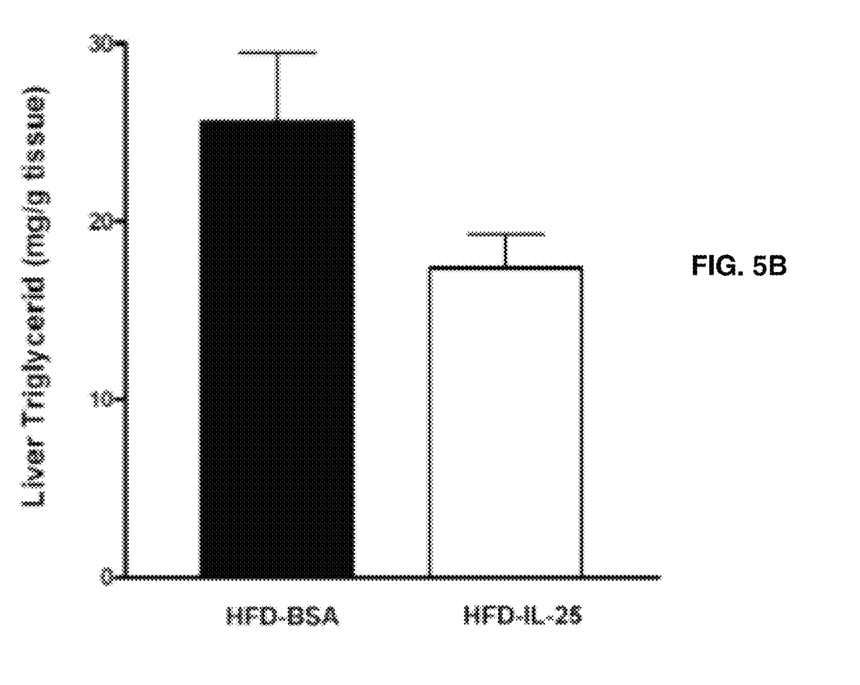
FIG. 5B: IL-25-induced decrease in liver triglyceride level of obese mice. *$p<0.05$ vs BSA, n=5 per group.

One of the major metabolic abnormalities associated with obesity is hepatic steatosis. Indeed, high fat diet obese mice had enlarged liver with elevated level of triglyceride compared with the lean mice (FIG. 5A). IL-25-treated obese mice had significantly smaller liver mass and lower liver triglyceride level compared with BSA-treated obese mice (FIGS. 5A and 5B). In normal control diet lean mice, both groups of IL-25- and BSA-treated mice had similar liver mass (FIG. 5A), but IL-25-treated mice had lower level of liver triglyceride compared with BSA group.

EXAMPLE 13

Figure 6:
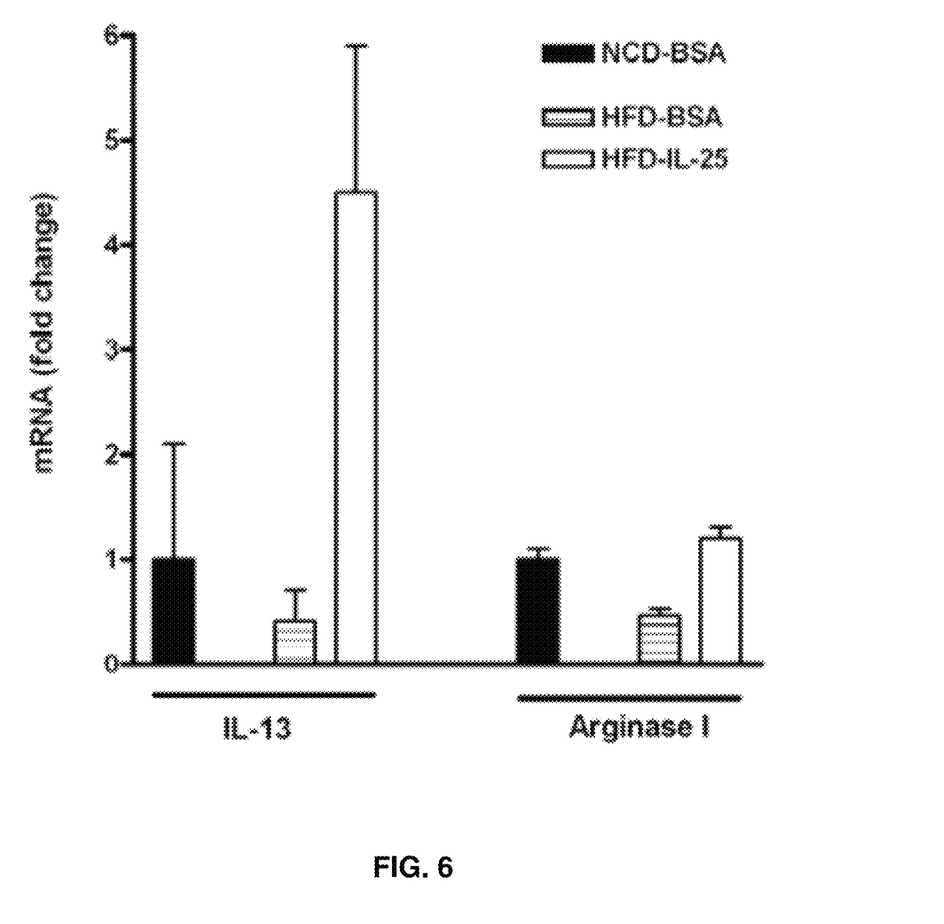
FIG. 6 shows that obesity is accompanied with low level of IL-13 expression and alternatively-activated macrophages (M2), while IL-25 treatment significantly up-regulated IL-13 expression and restored the level of alternatively-activated macrophages. *$p<0.05$ vs NCD, $\phi p<0.05$ vs BSA, n=5 per group.

Exogenous IL-25 Promoted Th2 Immunity Associated with Alternative Activation of Macrophages IL-25 is an immunoregulatory cytokine that promotes Th2 while inhibits Th1/T17, cytokine responses. To understand the mechanisms through which IL-25 regulate body weight and the associated metabolic syndrome, IL-25-induced changes in gene expression profiles of the major cytokines were analyzed. Exogenous IL-25 up-regulates the expression of major Th2 cytokines/mediators, IL-4, IL-13, GATA-3, while down-regulated Th1 cytokines, IL-12p40 and IL-23a, in the small intestine in mice. In addition, exogenous IL-25 induced intestinal macrophage differentiating towards M2 anti-inflammatory phenotype. In the present invention, the Th2 cytokine response and macrophage phenotype in adipose tissue and liver of the mice treated with IL-25 were further analyzed. In both obese epididymal fat and liver, IL-13 expression was significantly lower than that of the respective lean tissues (FIG. 6). IL-25 treatment up-regulated IL-13 expression in lean epididymal fat and liver, and did even more so in obese tissues (FIG. 6). Furthermore, IL-25 treatment in obese mice resulted in significant number of alternatively-activated macrophages (M2) in epididymal fat and liver, as it was shown by the increased expression of M2 marker arginase I, than that of obese mice treated with BSA (FIG. 6). Notably, the gene expression of pro-inflammatory cytokine TNF-α was dramatically down-regulated by IL-25 treatment in the tissues examined.

EXAMPLE 14

Macrophages Produced Th2 Cytokines and Played an Essential Role in Weight Loss in Response to IL-25 Stimulation The present invention clearly showed the protective effect of IL-25 against obesity and the associated metabolic syndrome and this effect is likely due to the ability of IL-25 to promote Th2 while inhibit Th1 cytokine responses. The specific cell type that responds to IL-25 to influence the immune response has not been fully understood. Recent studies identified four previously unidentified novel cell populations that may be involved in mediating IL-25 effect on Th2 immunity, whereas none of these cell types were shown to be able to respond to IL-25 directly. In response to enteric nematode infection that elicits a polarized Th2 immune response, macrophage is one of the major cell types that are recruited to the inflamed site at early stage of infection. Macrophages are essential to the protective Th2 host immunity against nematode infection. Given the important role of macrophages in both Th1 and Th2 immunities, whether macrophages can respond to IL-25 stimulation and produce Th2 cytokines was determined.

Figure 7A:
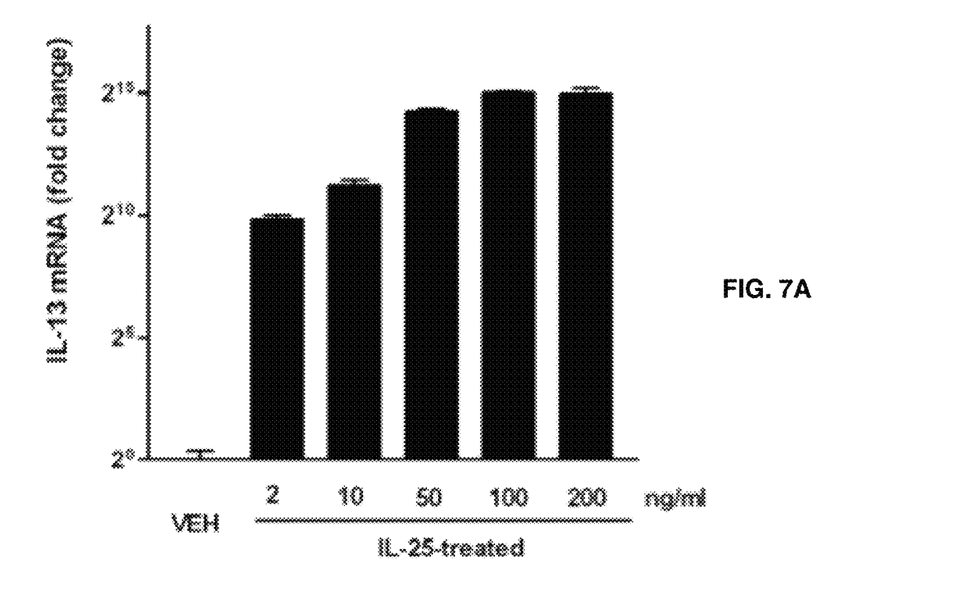
FIGS. 7A-7B: time- and concentration-dependent up-regulation of IL-13 mRNA
Figure 7B:
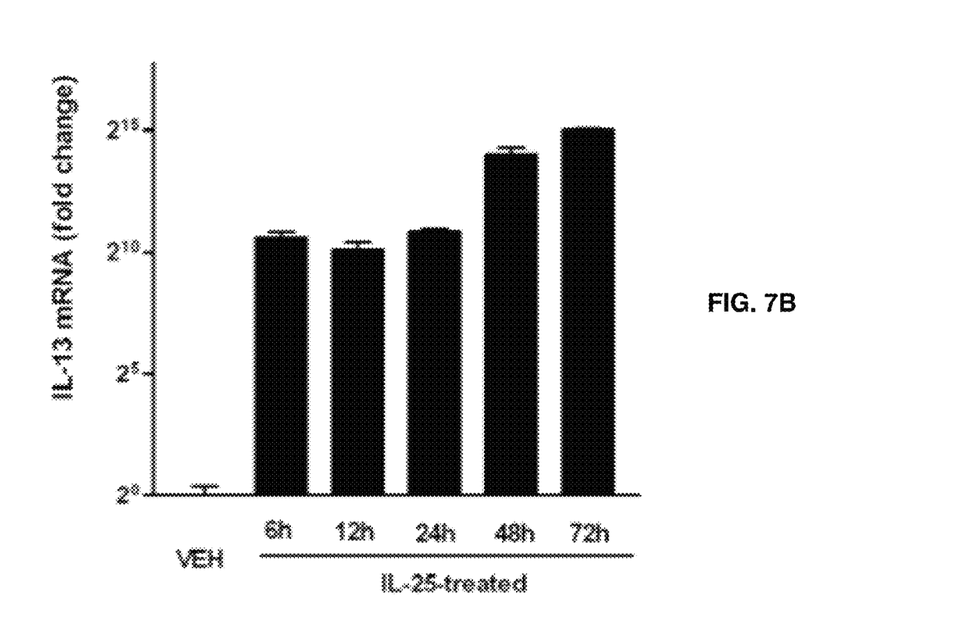
Figure 7C:
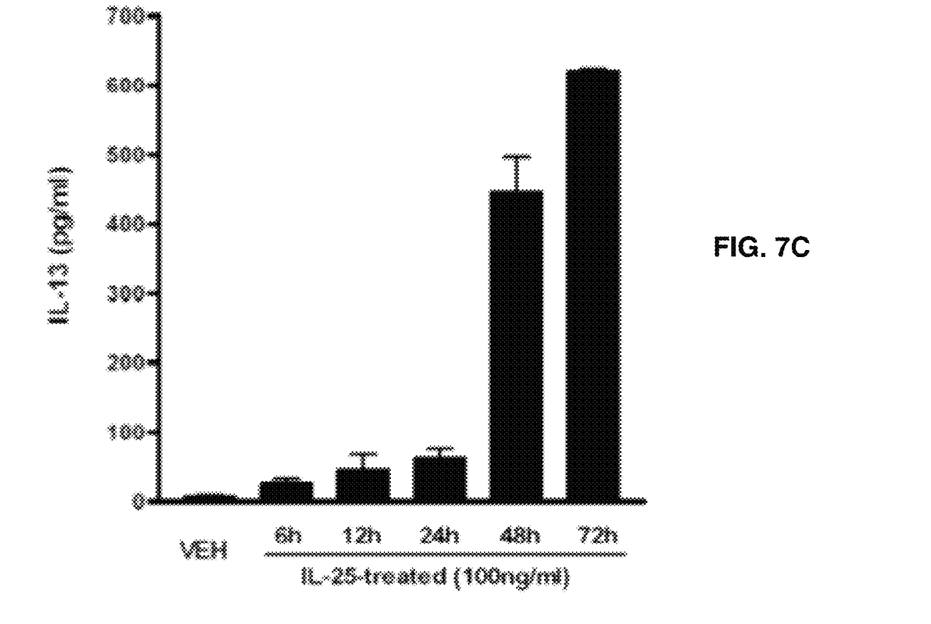
FIGS. 7C-7D: secretion of IL-13 in bone marrow-derived macrophages stimulated by IL-25.
Figure 7D:
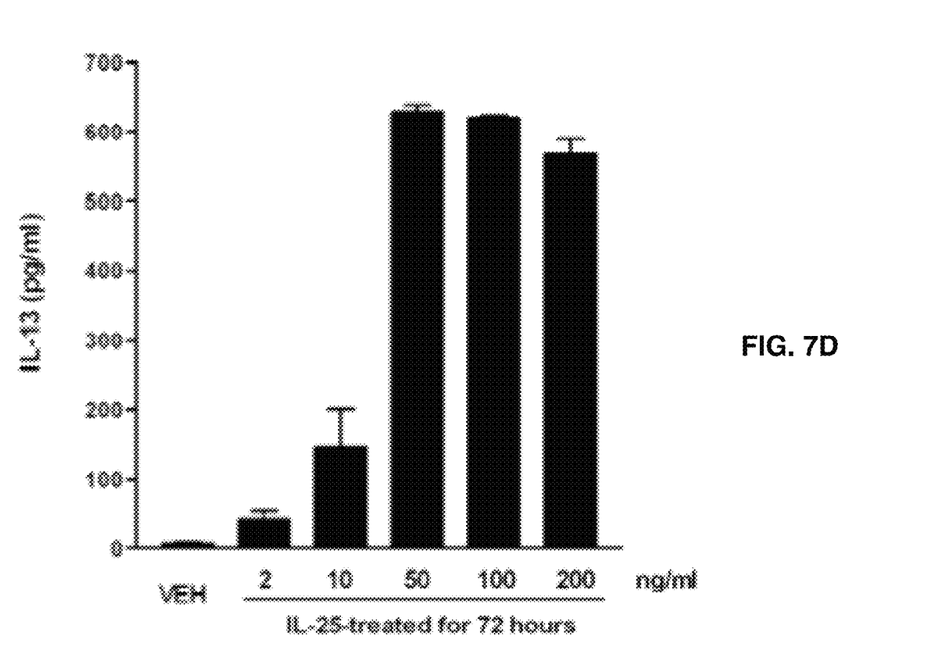

In vitro studies using bone marrow-derived macrophages (BMDM) were first performed. Real-time PCR showed the expression of IL-25R, IL-17RA and IL-17RB, is readily detectable in bone marrow-derived macrophages implying the macrophages are the potential IL-25-responsive cells. Bone marrow-derived macrophages were further treated with recombinant IL-25. IL-25 treatment induced a time- and concentration-dependent up-regulation of IL-13 mRNA in bone marrow-derived macrophages (FIGS. 7A and 7B). The IL-25 effect on IL-13 expression was confirmed by the ELISA results showing that IL-25-stimulated bone marrow-derived macrophages secreted IL-13 in a time- and concentration-dependent manner (FIGS. 7C and 7D). These results confirmed that macrophages are capable of responding to IL-25 and producing Th2 cytokines.

Figure 8A:
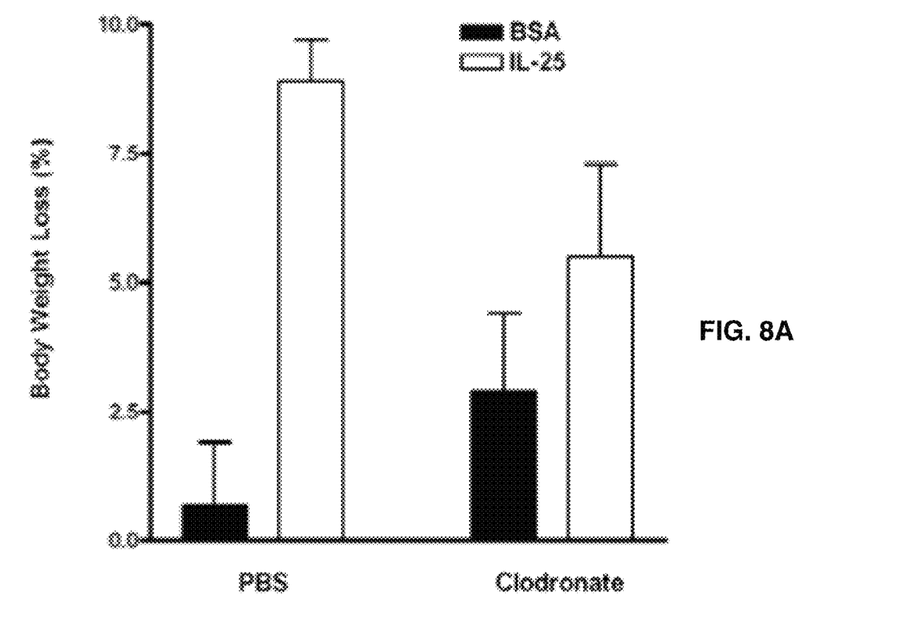
FIGS. 8A-8B shows the role of macrophages in IL-25-induced weight loss. IL-25 treatment induced weight loss in mice with macrophages, but not in mice depleted of macrophages (FIG. 8A); Mice adoptively transferred with IL-25-activated macrophages lost weight while the mice received control macrophages maintained their body weight (FIG. 8B). $P<0.05$ vs before treatment, n=5 per group.
Figure 8B:
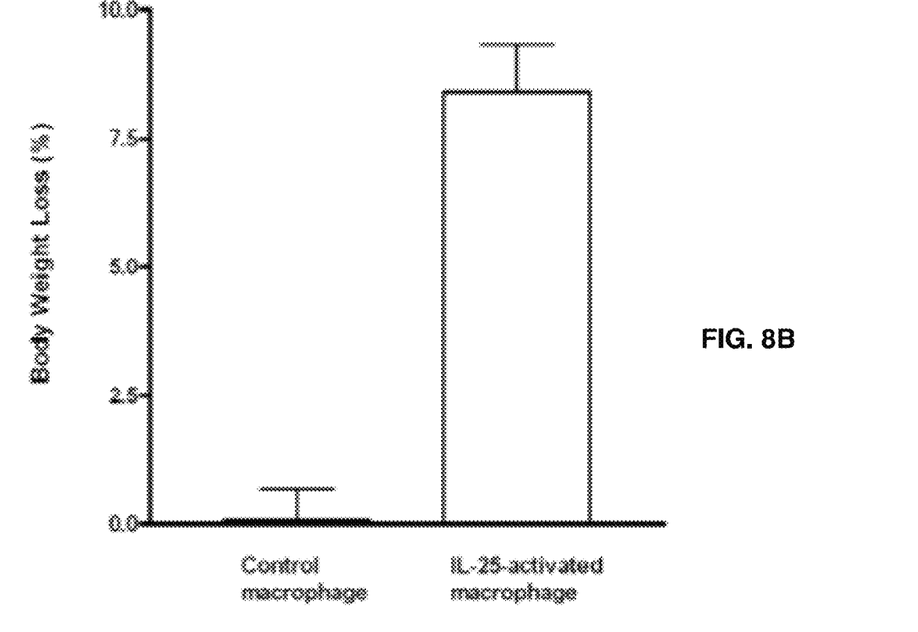

To determine whether macrophages play a role in IL-25-induced body weight loss, additional groups of 8-week old C57BL/6 mice fed with regular chow were used. Mice were administrated with Cl2MDP to deplete macrophages and then treated with IL-25. Consistent with the observation on high fat diet obese mice, these mice on regular diet treated with IL-25 for 4 days lost nearly 10% of the body weight (FIG. 8A). Cl2MDP injection of mice to deplete macrophages caused a slight weight loss in mice (~3%). However, IL-25 treatment in the mice depleted of macrophages did not lose additional weight, indicating macrophages are required for the weight losing effect of IL-25. Another piece of evidence on the role of macrophage in IL-25 effects on weight loss came from the mice adoptively transferred with IL-25-activated macrophages. These mice lost ~8% of the body weight while the mice received control macrophages maintained similar body weight during the entire course of experiment (FIG. 8B).

Discussion

IL-25 is emerging as a key regulator of inflammation because of its ability to promote Th2, while suppressing Th1 and Th17, cytokine responses. In the present study, exogenously administrated IL-25 resulted in significant weight loss of obese mice and improvement of the obesity-associated metabolic syndrome, while IL-25 deficiency in mice lead to a significant body weight gain. In addition, IL-25 treatment increased the gene expression of the anti-inflammatory cytokine IL-13 and the level of alternative activation of macrophages, but decreased the expression of pro-inflammatory cytokine TNFα. This research further established that macrophages are capable of responding to IL-25 to produce Th2 cytokines and that macrophages play an essential role in IL-25-induced weight loss in mice.

Obesity is associated with low grade inflammation and significant accumulation of inflammatory cells in the adipose tissue. Macrophages are the major cell types that can account up to 40% of the total obese adipose tissue cell content. These adipose tissue macrophages produce and secret variety of cytokines and chemokines, such as TNF-α, IL-6, IL-1α, CCL2, and MIF, which in turn activate the inflammatory pathways on insulin target cells, leading to insulin resistance.

Thus, the present invention provides a model of IL-25 effects on obesity and metabolic syndrome. IL-25 acts on macrophages to promote the alternative activation (M2) while inhibit the classical activation (M1) of macrophages, resulting in increased production of anti-inflammatory cytokines IL-4, IL-13, and IL-5, and decreased production of pro-inflammatory cytokines TNFα and IL-6. The altered cytokine/mediator profiles further influence the homeostasis of glucose and lipid metabolism, thus exert therapeutic effects against obesity and metabolic syndrome.

While the invention has been described with reference to certain particular embodiments, those skilled in the art will appreciate that various modifications may be made without departing from the spirit and scope of the invention. All publications mentioned in this specification are indicative of the level of those skilled in the art to which the invention pertains and each are incorporated by reference in its entirety.

What is claimed is:

1. A method for reducing the weight of an obese subject thereby improving glucose metabolism and glucose homeostasis, in a subject, comprising administering to a subject in need thereof a therapeutically effective amount of a pharmaceutical composition comprising interleukin-25.

2. The method of claim 1, wherein the pharmaceutical composition comprises one or more pharmaceutically acceptable carriers.

3. The method of claim 2, wherein the one or more pharmaceutically acceptable carriers is/are one or more liquid or solid fillers, diluents, excipients, solvents or encapsulating materials selected from the group consisting of: sugars, optionally lactose, glucose and/or sucrose; starches, optionally corn starch and/or potato starch; cellulose, and its derivatives, optionally sodium carboxymethyl cellulose, ethyl cellulose and/or cellulose acetate; powdered tragacanth; malt; gelatin; talc; excipients, optionally cocoa butter and/or suppository waxes; oils, optionally peanut oil, cottonseed oil, safflower oil, sesame oil, olive oil, corn oil and/or soybean oil; glycols, optionally propylene glycol; polyols, optionally glycerin, sorbitol, mannitol and/or polyethylene glycol; esters, optionally ethyl oleate and/or ethyl laurate; agar; buffering agents, optionally magnesium hydroxide and/or aluminum hydroxide; alginic acid; pyrogen-free water; isotonic saline; Ringer's solution; and phosphate buffer solutions.

4. The method of claim 1, wherein said composition administered to the subject in an amount of from about 0.5 mg/kg/day to about 1 mg/kg/day.

5. The method according to claim 1, wherein the subject is a human, a cat or a dog.

6. The method according to claim 5, wherein said human has a body mass index of at least about 25 kg/m$^2$.

7. The method according to claim 1, wherein said composition increases activation of macrophages in epididymal fat and liver.

* * * * *